United States Patent
Nishida

(10) Patent No.: US 8,500,779 B2
(45) Date of Patent: Aug. 6, 2013

(54) MINIMALLY-INVASIVE IMPLANT FOR OPENING AND ENLARGEMENT OF PROCESSUS SPINOSUS INTERSPACE

(75) Inventor: Kotaro Nishida, Hyogo (JP)

(73) Assignee: National University Corporation Kobe University, Hyogo (JP)

( * ) Notice: Subject to any disclaimer, the term of this patent is extended or adjusted under 35 U.S.C. 154(b) by 0 days.

(21) Appl. No.: 13/596,413

(22) Filed: Aug. 28, 2012

(65) Prior Publication Data
US 2013/0060286 A1 Mar. 7, 2013

Related U.S. Application Data

(63) Continuation of application No. 11/990,291, filed as application No. PCT/JP2006/315382 on Aug. 3, 2006, now Pat. No. 8,277,487.

(30) Foreign Application Priority Data

Aug. 11, 2005 (JP) .................................. 2005-232807

(51) Int. Cl.
*A61B 17/70* (2006.01)
(52) U.S. Cl.
USPC .......................................................... 606/249
(58) Field of Classification Search
USPC ..................... 606/246–249; 623/17.11–17.16
See application file for complete search history.

(56) References Cited

U.S. PATENT DOCUMENTS

| | | | | |
|---|---|---|---|---|
| 4,537,185 A | * | 8/1985 | Stednitz ........................ | 606/304 |
| 5,458,638 A | * | 10/1995 | Kuslich et al. ............... | 623/17.11 |
| 5,984,927 A | * | 11/1999 | Wenstrom et al. ........... | 606/329 |
| 6,093,207 A | * | 7/2000 | Pisharodi .................... | 623/17.16 |
| 6,096,081 A | | 8/2000 | Grivas et al. | |
| 6,562,039 B1 | * | 5/2003 | Wang et al. .................. | 606/247 |
| 6,648,916 B1 | | 11/2003 | McKay | |
| 7,273,498 B2 | * | 9/2007 | Bianchi et al. ............. | 623/17.16 |

(Continued)

FOREIGN PATENT DOCUMENTS

WO WO 2004/105656 12/2004

OTHER PUBLICATIONS

Tachiri et al., "Clinical Experience of Interspinous Process Space (Sten-X (tm)) Under Local Anesthesia for Lumbar Canal Stenosis", Sekitsui Sekizui Shinkei Shujutsu Shugi 6(1): 120-123, 2004.
Bono et al., "Interspinous Process Devices in the Lumbar Spine", J Spinal Disord Tech, vol. 20, No. 3, pp. 255-261 (May 2007).
Kim et al., "Interspinous Process Spacers", Journal of the American Academy of Orthopaedic Surgeons, vol. 15, No. 4, pp. 200-207 (Apr. 2007).

(Continued)

*Primary Examiner* — Jan Christopher Merene
*Assistant Examiner* — Steven Cotroneo
(74) *Attorney, Agent, or Firm* — Posz Law Group, PLC

(57) ABSTRACT

For minimally-invasive therapy for spinal canal stenosis, a therapeutic device capable of stationing an interspinous process spacer without the need of large skin incision or ligamentous tissue incision and also without the need of detaching of the paraspinal muscle from the spine. The interspinous process spacer includes a conoid screw region (2) to be screwed into a processus spinosus interspace; a spacer region (3) in the longitudinal direction of the screw region (2); head region (4) capable of free interlocking with a tool arbitrarily; and through-hole (5) passing through the axial centers of screw region (2), spacer region (3) and head region (4). The processus spinosus interspace is enlarged by screwing of the screw region (2) into the processus spinosus interspace. The spacer region (3) is pinched upon passing of the screw region (2) through the processus spinosus interspace to attain enlarging and fixing of adjacent processus spinosus interspaces.

19 Claims, 8 Drawing Sheets

U.S. PATENT DOCUMENTS

| | | | |
|---|---|---|---|
| 7,963,991 B2 * | 6/2011 | Conner et al. | 623/17.11 |
| 2001/0016743 A1 * | 8/2001 | Zucherman et al. | 606/61 |
| 2001/0039452 A1 * | 11/2001 | Zucherman et al. | 623/17.11 |
| 2005/0113929 A1 * | 5/2005 | Cragg et al. | 623/17.16 |
| 2005/0165398 A1 * | 7/2005 | Reiley | 606/61 |
| 2006/0265066 A1 * | 11/2006 | Zucherman et al. | 623/17.11 |
| 2009/0125066 A1 * | 5/2009 | Kraus et al. | 606/279 |

OTHER PUBLICATIONS

International Search Report of the International Searching Authority mailed on Oct. 17, 2006 for the corresponding international patent application No. PCT/JP2006/315382 (English translation enclosed).

* cited by examiner

22

30

Fig.3A  Fig.3B  Fig.3C
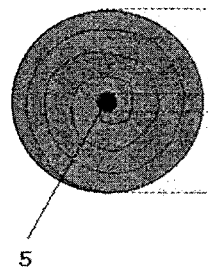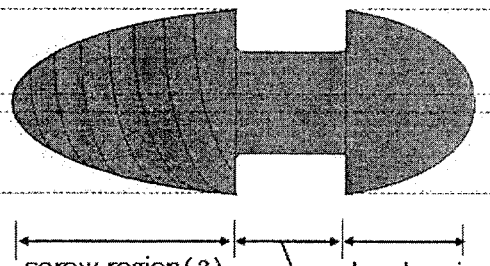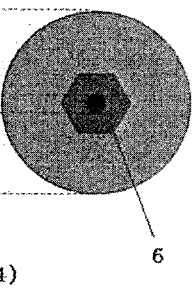
|← screw region (2) →|← →|← head region (4) →|
spacer region (3)
Fig.4A
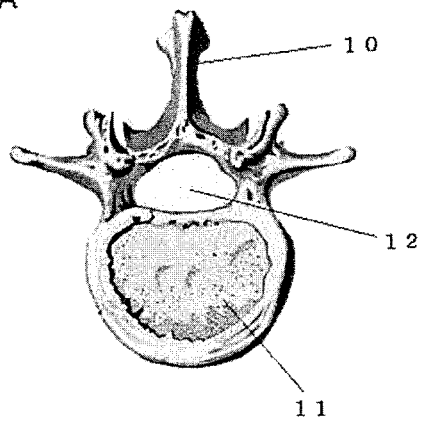
Fig.4B
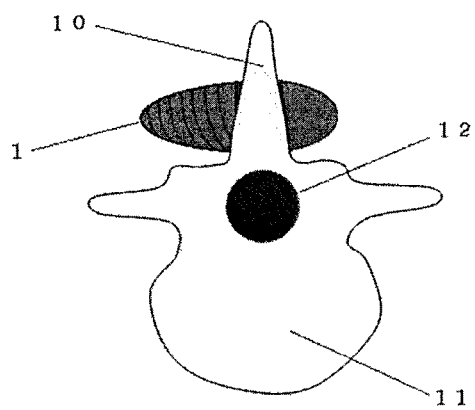

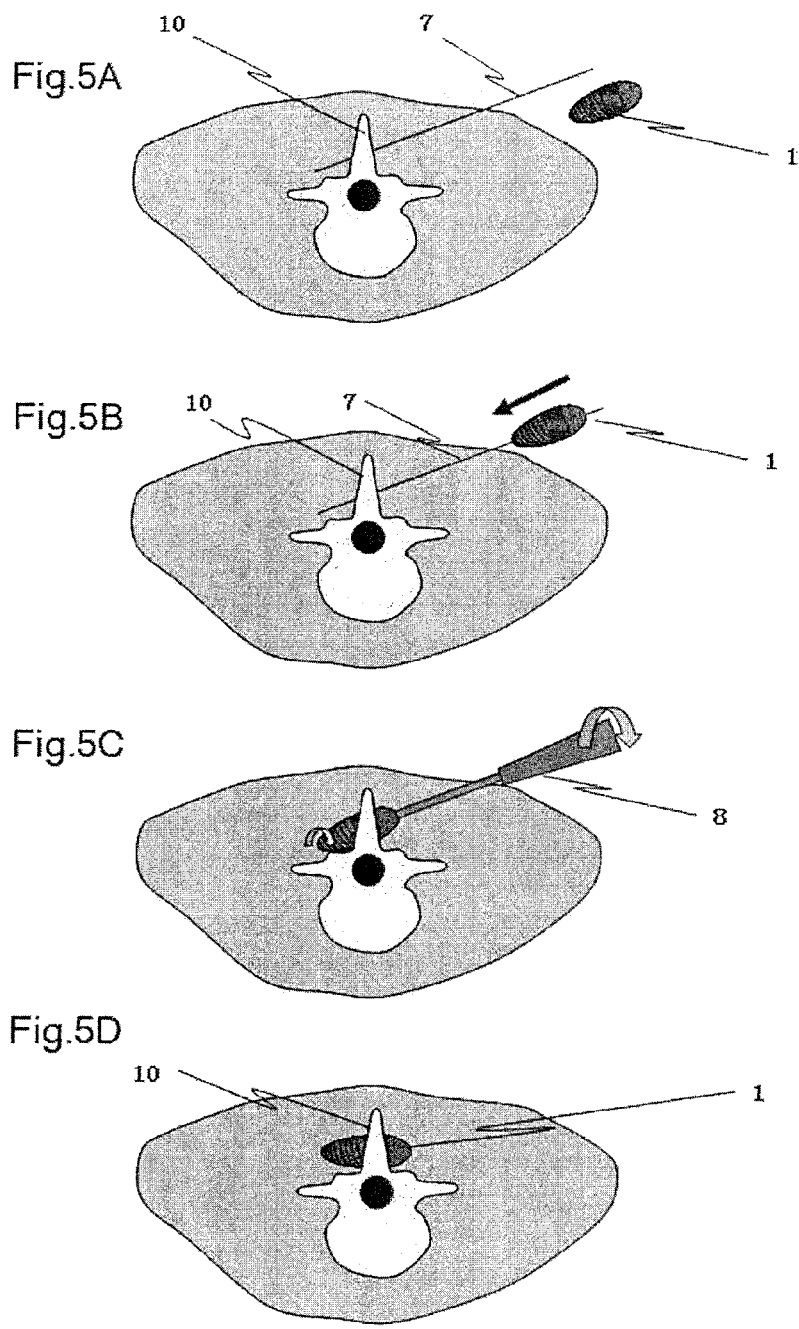

MINIMALLY-INVASIVE IMPLANT FOR OPENING AND ENLARGEMENT OF PROCESSUS SPINOSUS INTERSPACE

CROSS REFERENCE TO RELATED APPLICATIONS

The present application is a continuation of U.S. patent application Ser. No. 11/990,291 filed on Feb. 11, 2008, which is a U.S. national stage application of PCT/JP2006/315382 filed on Aug. 3, 2006, and claims priority to, and incorporates by reference, Japanese Patent Application No. 2005-232807 filed on Aug. 11, 2005.

BACKGROUND

The present invention relates to a minimally-invasive implant for the purpose of opening and enlargement of a processus spinosus interspace, and particularly an interspinous process spacer for enlarging the spinal canal.

The spinal canal is a cylindrical space in a vertical direction located in the center of a backbone (corpus vertebrae), and a spinal cord and cauda equina (nerve) are housed therein and protected firmly. Spinal canal stenosis where this spinal canal is stenosed due to various causes such as deformation of a bone, a cartilage or a ligament to press the nerve therein has become a major social problem as the number of patients has increased in conjunction with an aging society.

In particular, lumbar spinal canal stenosis refers to a state where the deformation and thickening of lumbar vertebra and intervertebral joints as well as deformation and bulging of the intervertebral, disc which is cartilage tissue, or hypertrophy of a ligament occurs and these make the spinal canal narrow to apply pressure or squeeze the nerves and blood vessels. This symptom is typified by a gait disorder such as neurogenic intermittent claudication, and this symptom is characterized in that a lower limb does not advance forward after walking for a few minutes and when taking a rest by crouching, subsequently the patient, can walk again. In addition, sciatic neuralgia, lower limb symptoms such as palsy, a cold sensation and a feeling of lassitude, lumbar pain and urinary bladder and rectal disorders (disorders of urination and defecation) and the like are lumbar and lower limb symptoms of lumbar spinal canal stenosis.

It has been known that lumbar and lower limb symptoms due to lumbar spinal canal stenosis are anatomically reduced and improved by anteflexion of the lumbar vertebra, e.g., crouching or riding a bicycle.

As conservative therapeutic methods which improve symptoms in daily life, physical therapies such as drug therapy of administering a drug which is a vasodilator drug or increases blood flow to a nerve root or a periphery of the cauda equina, an epidural block method, a radicular block method, an orthosis therapy of wearing a lumbar vertebra bending position corset to keep the lumbar portion at rest at the bending position, and an ultrasonic therapy and a hot pack therapy for improving pain relief, muscular spasticity and blood circulation are available.

When conservative therapy is ineffective and severe neurological disorder and intermittent claudication sustain, a surgical therapy countering this conservative therapy is available, and neurological decompression procedures such as a laminectomy and expanded fenestration have been conventionally performed. In the laminectomy and expanded fenestration, surgical invasion is applied to the patient to restore the lumbar vertebra stenosis site, and thus it is necessary to give general anesthesia to the patient. In this procedure, the patient is likely to be exposed to the risk of hemorrhaging and serious complications, and hospitalization for several days to several weeks is required for a patient after the operation. Therefore, this procedure heavily burdens the patient, and particularly when the patient is elderly, the symptom is sometimes further worsened.

However, in recent years, it has been reported that by stationing an interspinous process spacer in a minor surgical method, the effect of local lumbar anteflexion is obtained and satisfactory results are obtained (See International Application No. 2005-517467 and Sekitsui Sekizui Shinkei Shujutsu Shugi 6 (1):120-123, 2004, "Therapeutic experiences of lumbar spinal canal stenosis by interspinous process spacer (Sten-X™) performed under local anesthesia.").

Also, as the interspinous process spacer, the spacer inserted in the processus spinosus interspace using a guide pin and an obturator is publicly known (See WO 2005/072301).

Such a minimally invasive procedure can be performed, under a local anesthesia. Thus, a shorter period is needed for recovery, there is almost no hemorrhaging, the risk of serious complications is reduced, and therapeutic cost required for the patient is less. Therefore, it has been desired that spinal canal stenosis can be treated using the minimally invasive procedure.

As described above, it has been reported that by stationing the interspinous process spacer, the effect of local lumbar anteflexion is obtained and satisfactory results are obtained. A prior and existing spacer device used for this is described with reference to FIGS. 1A-1D. FIGS. 1A-1D show an entire schematic view and a use example of the prior and existing spacer device. FIG. 1A shows a completed view of an assembly of the spacer device, FIG. 1B shows an appearance where one wing region has been removed in the spacer device, FIGS. 1C and 1D show the appearances before and after attaching the spacer device. In the prior and existing spacer device 30, as shown in FIG. 1A, the wing regions 32 are constituted by pinching the spacer region 31, and as shown in FIG. 1B, one wing region is detachable.

Such a spacer device is disposed in the stenosed processus spinosus interspace as shown in FIG. 1D to enable enlarging and fixing the processus spinosus interspace.

In such a spacer device 30, as shown in FIGS. 2A-2D, a part of a back of a patient is cut open by means of surgical operation, the paraspinal muscle is detached, the processus spinosus and interspinous ligament are exposed (FIG. 2A), first a specialized device is inserted in the processus spinosus interspace to provide a hole in the processus spinosus interspace (FIG. 2B), subsequently the spacer device is inserted in the processus spinosus and screwed, into the processus spinosus interspace (FIG. 2C), and finally the wing region is placed from above and fixed with a screw (FIG. 2D). Thus, in the operation using this device, a minimal skin incision of about 3 cm or more is required, and it is necessary to detach the paraspinal muscle from the spine.

Such a procedure may be possible under local anesthesia but is difficult. Further surgical invasiveness is never minor.

In the interspinous process spacer disclosed in WO 2005/072301, in order to insert the spacer in the processus spinosus interspace, it is required to first insert the guide pin from, the skin incision site, subsequently the obturator is inserted which covers it to enlarge the processus spinosus interspace and finally insert the spacer. This obturator has a large diameter, thereby functioning to construct a path from the skin incision site to the processus spinosus interspace for inserting the spacer. However, in insertion of such an obturator, if the processus spinosus interspace is enlarged smoothly, it is required to insert the obturator by sequentially changing the diameter from small to large. Thus, the patient is heavily burdened and simultaneously the operator is burdened because of multiple procedures.

SUMMARY

Based on the above problems, the present invention aims at realising a more minimally invasive therapeutic method for spinal canal stenosis, and aims at providing a therapeutic device capable of simply stationing the interspinous process spacer without the need for a large skin incision and also without the need for detaching the paraspinal muscle from the spine.

The present inventor is a doctor specializing in organ treatment, has invented the interspinous process spacer according to the present invention through a wide range of clinical experience against spinal canal stenosis, and completed the present invention by producing and improving various prototype products. In order to achieve the above object, the interspinous process spacer according to the present invention including a conoid, screw region to be screwed into the processus spinosus interspace; a spacer region formed in a longitudinal direction of the screw region; and a head region capable of freely interlocking with a tool arbitrarily or freely attaching a coupling member arbitrarily; and has a through-hole in an axial center of the screw region, the spacer region and the head region.

According to the above constitution, the processus spinosus interspace is enlarged smoothly by utilizing an opening and enlarging force generated, when the screw region is screwed and inserted in the processus spinosus interspace, and the spacer region is pinched by passing the screw region through the processus spinosus interspace. Thus, finally the adjacent processus spinosus interspaces can be enlarged and fixed (the predetermined distance can be maintained in neutral or extension position). In addition, the head region capable of freely interlocking with the tool arbitrarily or freely attaching the coupling member arbitrarily means including, for example, a hole for a hexagon driver tool. Using the driver tool, it is possible to push the interspinous process spacer of the present invention by rotating from the small incision, site toward the internal processus spinosus interspace. By forming the through-hole in the axial center of the screw region and the spacer region, it becomes possible to couple with the guide member such as a guide wire through the through-hole. By the guide member, the interspinous process spacer of the present invention is guided to the processus spinosus interspace from the small incision site toward the internal processus spinosus interspace.

Here, it is preferable that, the screw region, of the interspinous process spacer according to the present invention has a substantially radial outer contour or a cone shape having a round tip end part. More preferably, the screw region of the interspinous process spacer according to the present invention is formed, into not a simple screw shape but an interference screw shape. The interspinous process spacer of the present invention proceeds in the dorsal skin and muscle of the patient by screw-rotating like a drill. By an obtuse angle and round cone-shape rather than an acute angle tip end part the screw region can reduce risk such as wrong insertion into the spinal canal.

In addition, the cross section of the spacer region of the interspinous process spacer according to the present invention can be circular, elliptical, substantially triangular, substantially rectangular or polygonal. As described above, by passing the screw region through the processus spinosus interspace; the spacer region is pinched to enlarge and fix the adjacent processus spinosus interspaces.

If the cross section of this spacer region is circular or elliptical, even when the screw region is passed through the processus spinosus interspace in any condition, it is possible to easily pinch the spacer region in the processus spinosus interspace. In addition, if the cross section of the spacer region is substantially triangular or substantially rectangular, the range joined to the adjacent processus spinosus is increased compared with the circular and elliptical cases. Thus, it is possible to stably pinch the spacer region in the processus spinosus interspace.

It is preferable that an outer shape of the entire interspinous process spacer according to the present invention is elliptical. From anatomical morphology, a wholly elliptical shape of the interspinous process spacer is easily housed between vertebral arches.

It is preferable that the diameter of the spacer region is larger than the diameters of the screw region and the head region in the diameter of the through-hole in the interspinous process spacer according to the present invention and the cross section of this through-hole in the longitudinal direction is substantially a spindle.

By making the hole for the guide wire of the interspinous process spacer spindle, i.e., making a middle thick, there is an advantage that the interspinous process spacer can be smoothly inserted even under the condition where the guide wire is not straight but bent.

It is also preferable that the screw region and the spacer region of the interspinous process spacer according to the present invention are composed of a ceramic material selected from alumina, zirconium, hydroxyapatite and calcium phosphate, a calcium phosphate based glass material having bioactivity, a resin material, a plastic material or a metal material selected from stainless steel, titanium and titanium alloy.

In addition, in the interspinous process spacer according to the present invention, the through-hole formed, in the axial center of the screw region and the spacer region is used as an insertion hole of the guide member. By coupling with the guide member introduced in the processus spinosus interspace via the dorsal skin in the patient, the interspinous process spacer can be easily guided to the processus spinosus interspace.

The method of percutaneously enlarging the processus spinosus interspace using the interspinous process spacer of the present invention is achieved by the following procedures. The processus spinosus interspace is enlarged by first identifying the location of spinal canal stenosis by radioscopic techniques such as an X-ray, and including (1) a stage of introducing the guide member from a posterolateral side via the dorsal skin in the patient to the above location; (2) a stage of inserting the guide member in the through-hole in the interspinous process spacer of the present invention; (3) a stage of inserting the screw region of the interspinous process spacer by rotating using a tool such as a driver; (4) a stage of enlarging the processus spinosus interspace by insertion of the screw region by rotating, subsequently passing the screw region through and pinching the spacer region in the processus spinosus interspace to fix the processus spinosus interspace; and (5) a stage of removing the guide member and the tool.

In particular, it is preferable that the interspinous process spacer of the present invention is embedded in the processus spinosus interspace of the adjacent thoracic vertebra and/or lumbar vertebra by the method of percutaneously enlarging the processus spinosus interspace described above.

In the interspinous process spacer of the present invention, by compositing the screw region and the spacer region, enlargement of the processus spinosus interspace and the insertion of the spacer can be achieved in one step. Further it becomes possible to insert and station the interspinous process spacer percutaneously even under local anesthesia. Thus, there is the effect that a minimally invasive operation simple in procedure can be performed. In particular, the spacer of the present invention far exceeds the prior and existing spacer device in that the interspinous process spacer can be stationed without the need for large skin incision or ligamentous tissue incision and also without the need for detaching the paraspinal muscle from the spine.

In addition, an early effect after operation can be anticipated, an outpatient operation is thought to be possible, and it is possible to further reduce temporal, physical and financial burdens on the patient.

BRIEF DESCRIPTION OF THE DRAWINGS

FIGS. 3A-C show an example of the interspinous process spacer according to the present invention where FIG. 3A is a front view, FIG. 3B is a side view and FIG. 3C a rear view.

FIG. 4A is a cross sectional view of spinal canal, and FIG. 4B is a diagrammatic view showing the interspinous process spacer of the present invention mounted in the spinal canal.

FIGS. 5A-5D are diagrammatic views showing procedures of an operation using the interspinous process spacer of the present invention.

DETAILED DESCRIPTION OF THE PREFERRED EMBODIMENTS

Figure 1A:
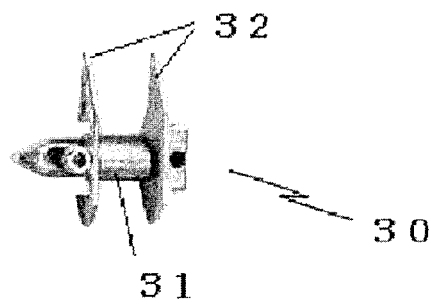
FIGS. 1A and 1B are perspective views of the prior and existing spacer device.
Figure 1B:
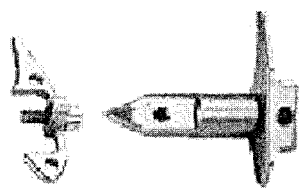
Figure 1C:
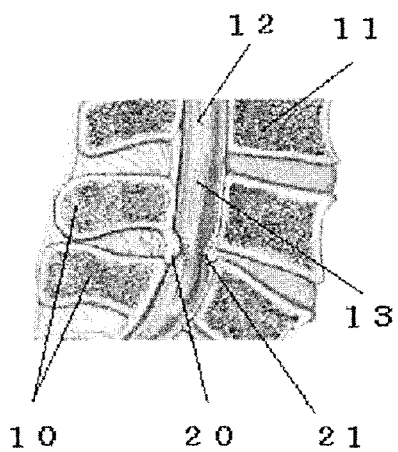
FIGS. 1C and 1D are cross-sectional views showing the prior and existing spacer device in use in the processus spinosus interspace.
Figure 1D:
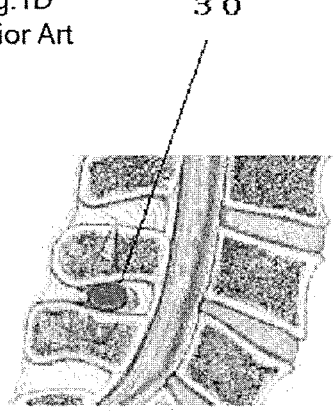
Figure 2A:
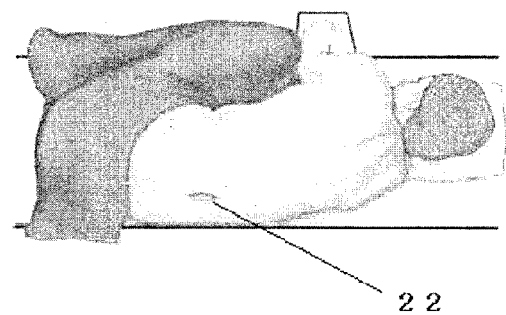
FIGS. 2A-2D show a surgical operation using the prior and existing spacer device.
Figure 2B:
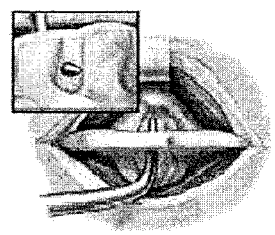
Figure 2C:
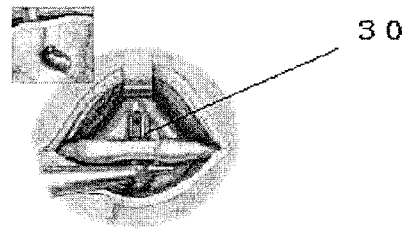
Figure 2D:
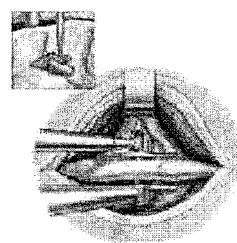

Embodiments of the present invention will be described, in detail below with reference to the drawings.

FIGS. 3A-C show the shape of the interspinous process spacer according to the present invention. As is shown in FIG. 3B, the interspinous process spacer of the present invention is constituted, by including the conoid screw region 2; the spacer region 3 formed in the longitudinal direction of the screw region; the head region 4 including the hole 6 for the hexagon driver which can interlock with the hexagon driver and the insertion hole 5 for the guide wire penetrating in the axial center of the screw region 2, the spacer region 3 and the head portion 4. As shown in FIG. 3B, it is preferable that the outer contour of the shape in the cross sectional view of the interspinous process spacer is substantially elliptical. From clinical experience, it was found to be easily housed in vertebral arches.

Here, the screw region 2 of the interspinous process spacer has a substantially radial outer contour. This is because when the screw region 2 passes through the processus spinosus interspace, the processus spinosus interspace can be enlarged by the radial outer contour and the spacer region 3 is easily fitted in the processus spinosus interspace. Further, the cross section of the spacer region 3 in the interspinous process spacer is formed into circular shape, and the spacer region is wholly cylindrical. This is because the spacer region 3 can be stably fitted in the processus spinosus interspace even when the screw region 2 passes through the processus spinosus interspace at any angle.

By including the hole 6 for the hexagon driver, the interspinous process spacer of the present invention can be pushed from the small incision site toward the internal processus spinosus interspace by rotating the interspinous process spacer of the present invention using a driver tool. By including the insertion hole 5 for the guide wire, the interspinous process spacer of the present invention can be coupled with the guide wire, and by inserting the guide wire from the small incision site toward the internal processus spinosus interspace, the spacer can be guided to the processus spinosus interspace along the guide wire.

In FIG. 4A, a cross sectional view of the spinal canal is shown. In FIG. 4A, 10 represents processus spinosus, 11 represents vertebral body and 12 represents vertebral foramen. As shown in FIG. 4B, finally the spacer region of the interspinous process spacer is pinched between adjacent processus spinosus 11.

In FIGS. 5A-5D, the procedure in the operation using the interspinous process spacer according to the present invention is shown. First, as shown in FIG. 5A, the guide wire 7 is inserted from the dorsal small incision site in the patient to insert the guide wire 7 between the processus spinosus 10. Subsequently as shown, in FIG. 5B, one end of the inserted guide wire 7 is passed through the insertion hole for the guide wire penetrating in the axial center of the interspinous process spacer according to the present invention. And, as shown in FIG. 5C, the hexagon driver 8 is inserted in the hole for the hexagon driver provided in the head region of the interspinous process spacer 1, and the interspinous process spacer 1 is screwed in the processus spinosus interspace using a hexagon driver 8. At that time, the processus spinosus interspace can be smoothly enlarged by the radial outer contour of the screw region of the interspinous process spacer 1. And as shown in FIG. 5O, when the screw region of the interspinous process spacer 1 is passed through the processus spinosus 10, the spacer region of the interspinous process spacer 1 is pinched, and the processus spinosus interspace can be stably enlarged and fixed.

Figure 6A:
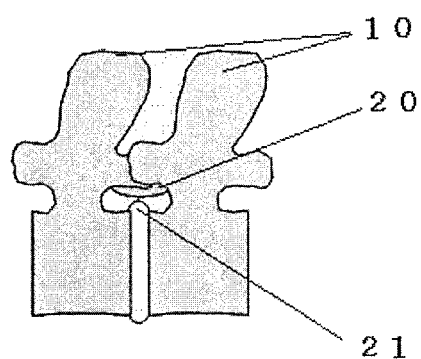
FIG. 6A is a diagrammatic side cross sectional view of spinal canal.
Figure 6B:
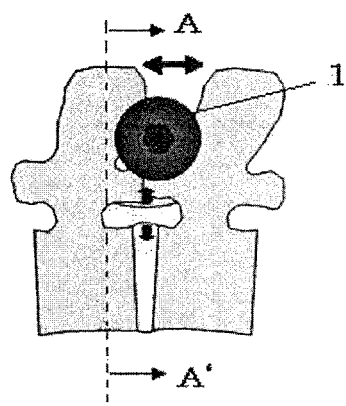
FIG. 6B is a similar view showing the interspinous process spacer according to the present invention mounted in the spinal canal.
Figure 6C:
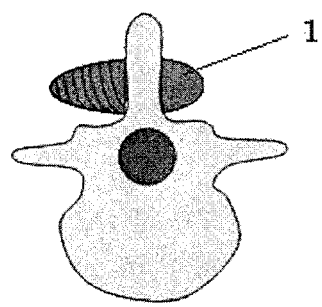
FIG. 6C is a diagrammatic cross sectional view taken along the plane A-A'.

FIG. 6A shows a side cross sectional view of the spinal canal, and FIGS. 6B and 6C show the appearances where the interspinous process spacer according to the present invention has been loaded in the spinal canal. In the figure, 20 represents a hypertrophic yellow ligament and 21 represents the bulging of intervertebral disc.

It can be seen that the spinal canal is stenosed in FIG. 6A and as shown in FIG. 6B, the spinal, canal has been, enlarged by the interspinous process spacer according to the present invention.

The present invention can be executed by a specific method other than the method, described herein above without departing from the scope and the essential features of the present invention. In one embodiment, the interspinous process spacer according to the present invention and the method of percutaneously enlarging the processus spinosus interspace are used for enlarging and fixing the adjacent processus spinosus interspaces. However, the present invention may be applied to making a space in other tissue in the body (enlarging and fixing the distance between the bones). The present embodiment is to be considered in all respects without being limited, and all changes which occur within the meanings of claims and the equivalent scope are intended to be included therein.

Example 1

Figure 7:
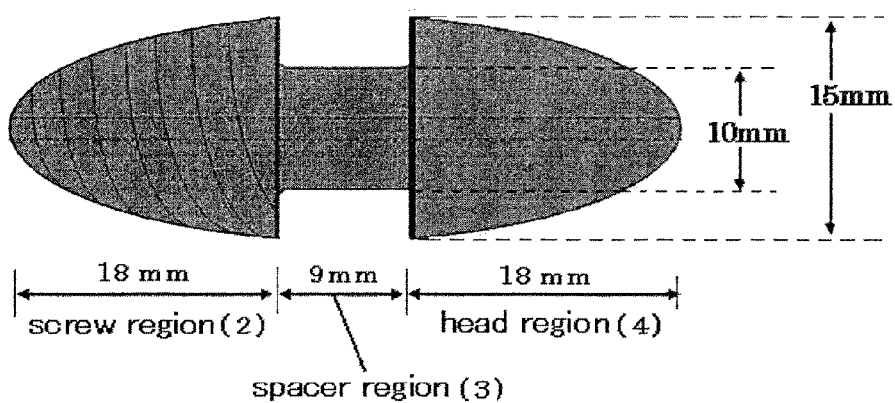
FIG. 7 is a diagrammatic side view of the interspinous process spacer of Example 1.

An outline drawing of the interspinous process spacer in Example 1 is shown in FIG. 7. In the interspinous process spacer in Example 1, the spacer region 3 has been made by removing the center of an elliptical sphere made from titanium and the screw region 2 has been made by threading one end section of the spacer.

The dimensions (length and diameter) of the spacer region 3 have some variation depending on the condition of the processus spinosus interspace in a diseased part, and FIG. 7 consistently shows one example of the dimensions.

Figure 8:
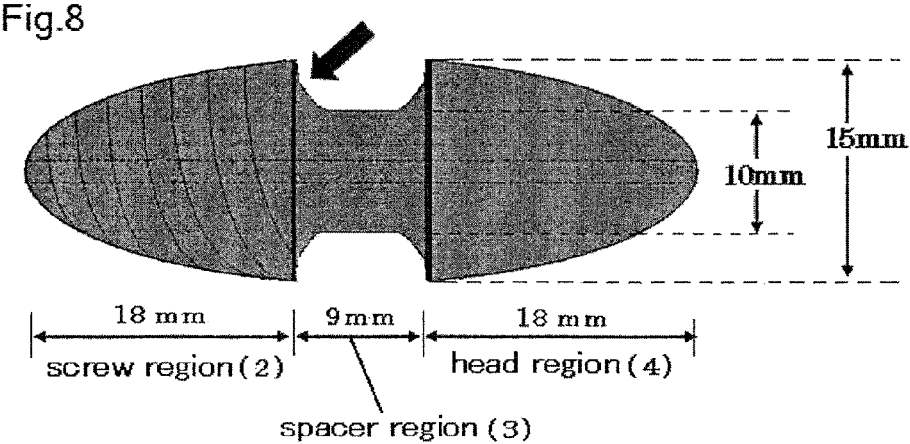
FIG. 8 is a diagrammatic side view showing the interspinous process spacer made without a step.
Figure 9A:
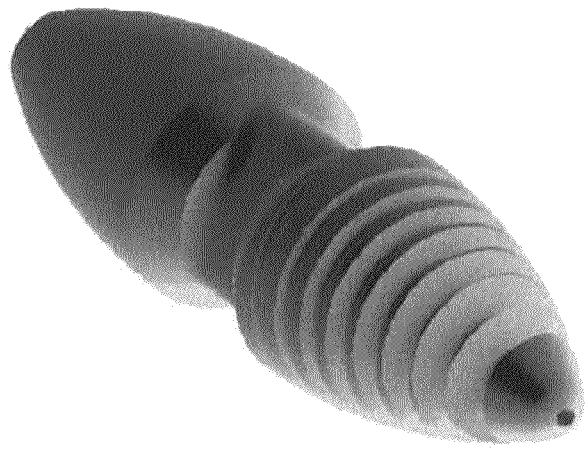
FIG. 9A is a perspective view of the interspinous process spacer in Example 1.
Figure 9B:
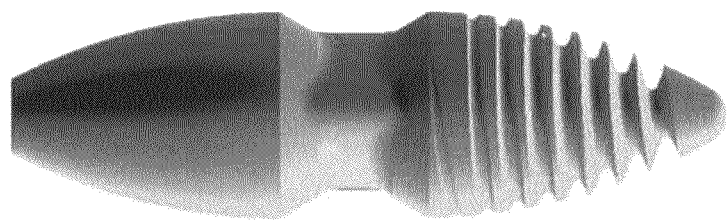
FIG. 9B is a side view of the interspinous process spacer of FIG. 9A.
Figure 9C:
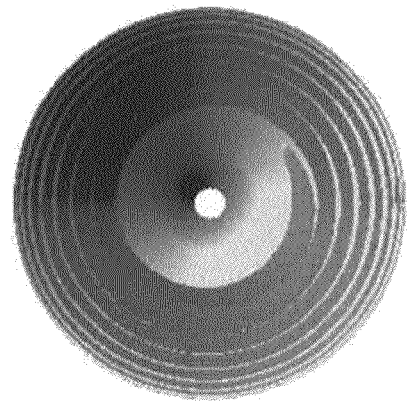
FIG. 9C is a right end view of the interspinous process spacer of FIG. 9B.
Figure 9D:
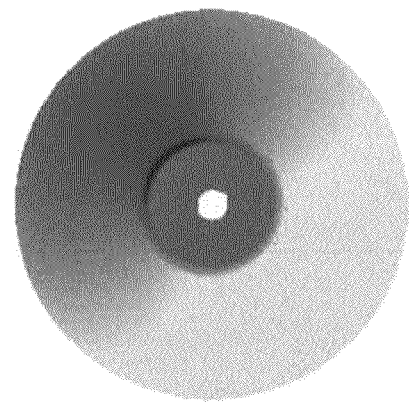
FIG. 9D is a left end view of the interspinous process spacer of FIG. 9B.

The tip end part of the screw region 2 has been formed into a hemisphere in FIG. 7, but this may be formed into a cone shape having a round tip. In addition, a joint of the screw region 2 and the spacer region 3 has produced a step in FIG. 7, but as shown by an arrow in FIG. 8, an end-to-side of the spacer region 3 may be extended to a coronal side of the screw region 2 to be made adjacent without the step. In addition, a screw pitch in the screw region 2 is about 1 to 2 mm, and the screw wing is protruded from the radial outer contour of the screw region 2. FIGS. 9A-9D include a perspective view, a plane view, a right side view and a left side view of the interspinous process spacer in Example 1, respectively.

Next, an insertion procedure protocol of the interspinous process spacer of the present invention will be described. The targeted patient is a patient diagnosed with lumbar spinal canal stenosis who exhibits a so-called intermittent claudication, and whose symptoms are reduced by anteflexion of lumbar vertebra and whose arteriosclerotic obliteration has been denied. However, extreme lumbar kyphos, epiphysis and lateral curvature are to be excluded, and severe osteoporosis is also to be excluded.

As a measurement and plan before the operation, the size (diameter) of the spacer region of the interspinous process spacer is determined on an X-ray side image of a sitting position and a lumbar maximum anteflexion position (actual measurement). Subsequently, the full length of the interspinous process spacer is determined by measuring the distance between superior articular processes on a standing position X-ray image or CT image. Also, an entry point and an angle of the guide pin are measured on the CT image.

The protocol of the actual operation is shown by the following procedures (a) to (i).

(a) Radioscopy (image) is performed in a knee/chest position.

(b) The entry point of the guide pin is determined according to the measurement. A horizontal incision of about 1 cm is made on the skin at the determined position.

(c) The guide pin is inserted. It is confirmed by an radioscopy (image) that the guide pin has passed the portion as close as possible to the base of the targeted processus spinosus interspace and the tip end of the pin has passed over an opposed intervertebral facet joint.

(d) A small incision is given to fascias according to the skin incision, and the interspinous process spacer of the present invention is inserted along the guide pin.

(e) The interspinous process spacer is allowed to proceed using the driver.

(f) When the tip end part of the interspinous process spacer reaches the processus spinosus interspace, the spacer is inserted by adding a rotational force to the driver. The screw region proceeds by enlarging the processus spinosus interspace and the spacer region is pinched, thereby the interspinous process spacer is fixed.

(g) The driver is changed to a multi-axial type (the tip has a paper-covered lamp shape), the guide pin is removed and subsequently the position (slope) of the interspinous process spacer is adjusted.

(h) The position of the interspinous process spacer is confirmed again by radioscopy (image), and subsequently the driver is removed.

(i) The fascias and skin are sewn to finish the operation.

The interspinous process spacer according to the present invention is anticipated to be utilized as a medical device useful for surgical therapy of spinal canal stenosis.

DESCRIPTION OF REFERENCE CHARACTERS

1. Interspinous process spacer according to the present invention
2. screw region
3. spacer region
4. head region
5. insertion hole for guide wire
6. hole for hexagon driver
7. guide wire
8. hexagon driver
10. processus spinosus
11. vertebral body (lumbar vertebra)
12. vertebral foramen
13. nerve root
20. hypertrophic yellow ligament
21. bulging of intervertebral disc
22. small incision site
30. prior and existing spacer device (spacer device shown, in the Sekitsui Sekizui Shinkei Shujutsu Shugi publication)
31. spacer region
32. wing region

What is claimed is:

1. An interspinous process spacer having a longitudinal center axis, and being adapted to rest between adjacent processus spinosus such that the longitudinal center axis is transverse to a spine of a patient, comprising:
   a substantially conoid screw region;
   a head region;
   a spacer region; and
   a through-hole, wherein
   the screw region
      forms one end of the interspinous process spacer in a longitudinal direction along the longitudinal center axis,
      includes a rounded distal portion and a proximal portion, and
      is adapted to be screwed into a processus spinosus interspace such that the distal portion enters the processus spinosus interspace prior to the proximal portion, an outer contour of the screw region tapering over a majority of the distance from the proximal end of the screw region to the distal end of the screw region;

the head region
forms another end of the interspinous process spacer in the longitudinal direction,
includes a driver hole coaxial with the longitudinal center axis, and
is adapted to couple with a tool to rotate the interspinous process spacer about the longitudinal center axis;
the spacer region
is formed in between the screw region and the head region in the longitudinal direction, a length of the spacer region in the longitudinal direction being greater than a width, measured in the same direction of inserting the spacer, of each of the adjacent processus spinosus;
the through-hole
extends along the longitudinal center axis and through the screw region, the spacer region, and the head region with exterior openings at far ends of the screw region and head region; and
when the screw region is screwed and inserted into the processus spinosus interspace, the processus spinosus interspace between the adjacent processus spinosus is enlarged, and the spacer region is pinched by the adjacent processus spinosus such that the spacer is secured in the processus spinosus interspace.

2. An interspinous process spacer having a longitudinal center axis, and being adapted to rest between adjacent processus spinosus such that the longitudinal center axis is transverse to a spine of a patient, comprising:
a substantially conoid screw region;
a head region;
a spacer region; and
a through-hole, wherein
the screw region
forms one end of the interspinous process spacer in a longitudinal direction along the longitudinal center axis,
includes a rounded distal portion and a proximal portion, and
is adapted to be screwed into a processus spinosus interspace such that the distal portion enters the processus spinosus interspace prior to the proximal portion, an outer contour of the screw region tapering over a majority of the distance from the proximal end of the screw region to the distal end of the screw region;
the head region
forms another end of the interspinous process spacer in the longitudinal direction,
includes a driver hole coaxial with the longitudinal center axis, and
is adapted to couple with a tool to rotate the interspinous process spacer about the longitudinal center axis;
the spacer region
is formed in between the screw region and the head region in the longitudinal direction, and
is smaller, as measured radially from the longitudinal center axis, than portions of the head region and the screw region that are adjacent to the spacer region, a length of the spacer region in the longitudinal direction being greater than a width, measured in the same direction of inserting the spacer, of each of the adjacent processus spinosus;
the through-hole
extends along the longitudinal center axis and through the screw region, the spacer region, and the head region with exterior openings at far ends of the screw region and head region; and
when the screw region is screwed and inserted into the processus spinosus interspace, the processus spinosus interspace between the adjacent processus spinosus is enlarged, and the spacer region is pinched by the adjacent processus spinosus such that the spacer is secured in the processus spinosus interspace.

3. The interspinous process spacer according to claim 2, wherein
the interspinous process spacer, when inserted in the processus spinosus interspace, is a single, unitary, integral device that maintains a predetermined distance between adjacent processus spinosus.

4. The interspinous process spacer according to claim 2, wherein
the screw region, the head region, and the spacer region are arranged and shaped such that an outer contour of the interspinous process spacer has a generally elliptical shape, a major axis of the elliptical shape corresponding to the longitudinal center axis.

5. The interspinous process spacer according to claim 2, wherein
the head region is substantially conoid.

6. The interspinous process spacer according to claim 2, wherein
the screw region, the head region, and the spacer region are arranged and shaped to be generally symmetrical about a plane that passes through a center of the spacer region and perpendicular to the longitudinal center axis.

7. The interspinous process spacer according to claim 2, wherein
a cross section of the spacer region is circular, elliptical, substantially triangular, substantially rectangular or polygonal.

8. The interspinous process spacer according to claim 2, wherein
the screw region and spacer region are composed of a ceramic material selected from alumina, zirconium, hydroxyapatite and calcium phosphate, a calcium phosphate based glass material having bioactivity, a resin material, a plastic material or a metal material selected from stainless steel, titanium and titanium alloy.

9. The interspinous process spacer according to claim 2, wherein
the spacer region includes an annular recess for receiving a processus spinosus.

10. The interspinous process spacer according to claim 2, wherein
a length of the screw region in the longitudinal direction is greater than a length of the spacer region in the longitudinal direction.

11. An interspinous process spacer having a longitudinal center axis, and being adapted to rest between adjacent processus spinosus such that the longitudinal center axis is transverse to a spine of a patient, comprising:
a substantially conoid screw region;
a substantially conoid head region;
a spacer region; and
a through-hole, wherein
the screw region
forms one end of the interspinous process spacer in a longitudinal direction along the longitudinal center axis,
includes a rounded distal portion and a proximal portion, and
is adapted to be screwed into a processus spinosus interspace such that the distal portion enters the processus spinosus interspace prior to the proximal portion, an outer contour of the screw region tapering over a majority of the distance from the proximal end of the screw region to the distal end of the screw region;

the head region forms another end of the interspinous process spacer in the longitudinal direction, includes a driver hole coaxial with the longitudinal center axis, and is adapted to couple with a tool to rotate the interspinous process spacer about the longitudinal center axis;

the spacer region is formed in between the screw region and the head region in the longitudinal direction;

is smaller, as measured radially from the longitudinal center axis, than portions of the head region and the screw region that are adjacent to the spacer region, a length of the spacer region in the longitudinal direction being greater than a width, measured in the same direction of inserting the spacer, of each of the adjacent processus spinosus;

the screw region, the head region, and the spacer region are arranged and shaped such that an outer contour of the interspinous process spacer has a generally elliptical shape, a major axis of the elliptical shape corresponding to the longitudinal center axis;

the through-hole extends along the longitudinal center axis and through the screw region, the spacer region, and the head region with exterior openings at far ends of the screw region and head region; and when the screw region is screwed and inserted into the processus spinosus interspace, the processus spinosus interspace between the adjacent processus spinosus is enlarged, and the spacer region is pinched by the adjacent processus spinosus such that the spacer is secured in the processus spinosus interspace.

12. The interspinous process spacer according to claim 11, wherein the interspinous process spacer, when inserted in the processus spinosus interspace, is a single, unitary, integral device that maintains a predetermined distance between adjacent processus spinosus.

13. The interspinous process spacer according to claim 11, wherein the screw region, the head region, and the spacer region are arranged and shaped to be generally symmetrical about a plane that passes through a center of the spacer region and perpendicular to the longitudinal center axis.

14. The interspinous process spacer according to claim 11, wherein a cross section of the spacer region is circular, elliptical, substantially triangular, substantially rectangular or polygonal.

15. The interspinous process spacer according to claim 11, wherein the screw region and spacer region are composed of a ceramic material selected from alumina, zirconium, hydroxyapatite and calcium phosphate, a calcium phosphate based glass material having bioactivity, a resin material, a plastic material or a metal material selected from stainless steel, titanium and titanium alloy.

16. The interspinous process spacer according to claim 11, wherein the spacer region includes an annular recess for receiving a processus spinosus.

17. The interspinous process spacer according to claim 11, wherein a length of the screw region in the longitudinal direction is greater than a length of the spacer region in the longitudinal direction.

18. The interspinous process spacer according to claim 11, wherein the interspinous process spacer, when inserted in the processus spinosus interspace, is a single, unitary, integral device that maintains a predetermined distance between adjacent processus spinosus;

a cross section of the spacer region is circular, elliptical, substantially triangular, substantially rectangular or polygonal;

the spacer region includes an annular recess for receiving a processus spinosus; and a length of the screw region in the longitudinal direction is greater than a length of the spacer region in the longitudinal direction.

19. The interspinous process spacer according to claim 11, wherein the interspinous process spacer, when inserted in the processus spinosus interspace, is a single, unitary, integral device that maintains a predetermined distance between adjacent processus spinosus;

a cross section of the spacer region is circular, elliptical, substantially triangular, substantially rectangular or polygonal;

the spacer region includes an annular recess for receiving a processus spinosus;

a length of the screw region in the longitudinal direction is greater than a length of the spacer region in the longitudinal direction; and the screw region, the head region, and the spacer region are arranged and shaped to be generally symmetrical about a plane that passes through a center of the spacer region and perpendicular to the longitudinal center axis.

* * * * *